(12) United States Patent
Horikawa

(10) Patent No.: US 9,931,130 B2
(45) Date of Patent: Apr. 3, 2018

(54) MEDICAL INSTRUMENT

(71) Applicant: Kaoru Horikawa, Fukui (JP)

(72) Inventor: Kaoru Horikawa, Sabae (JP)

(73) Assignee: CHARMANT CO., LTD., Sabae Shi, Fukui (JP)

( * ) Notice: Subject to any disclaimer, the term of this patent is extended or adjusted under 35 U.S.C. 154(b) by 328 days.

(21) Appl. No.: 14/651,900

(22) PCT Filed: Dec. 13, 2012

(86) PCT No.: PCT/JP2012/007968
§ 371 (c)(1),
(2) Date: Jun. 12, 2015

(87) PCT Pub. No.: WO2014/091523
PCT Pub. Date: Jun. 19, 2014

(65) Prior Publication Data
US 2015/0313618 A1 Nov. 5, 2015

(51) Int. Cl.
*A61B 17/28* (2006.01)
*A61B 17/3201* (2006.01)
(Continued)

(52) U.S. Cl.
CPC ...... *A61B 17/2812* (2013.01); *A45D 26/0066* (2013.01); *A61B 17/30* (2013.01);
(Continued)

(58) Field of Classification Search
CPC . A61B 17/2812; A61B 17/30; A61B 17/3201; A61B 2017/2918;
(Continued)

(56) References Cited

U.S. PATENT DOCUMENTS 3,577,991 A * 5/1971 Wilkinson ........... A61B 17/062
606/206
3,651,811 A * 3/1972 Hildebrandt ....... A61B 17/3201
606/51
(Continued)

FOREIGN PATENT DOCUMENTS

CN 102686172 A 9/2012
DE 10125149 A1 12/2002
(Continued)

OTHER PUBLICATIONS

Search Report for EP Application No. 12889912, dated Jun. 20, 2016.
(Continued)

*Primary Examiner* — Julian W Woo
(74) *Attorney, Agent, or Firm* — Hauptman Ham, LLP; Martin J. Cosenza

(57) ABSTRACT

A medical instrument effectively suppresses a situation in which the edge of a blade springs immediately after completion of incision, excision, or the like. The medical instrument (1) includes manipulation members (14) that are held by a user, elastic members (11) that are respectively secured on one end of the manipulation members, and intersect each other at one end thereof, and opening-closing members (15) that are respectively secured on the other end of the manipulation members (14), and intersect each other at a pivot (13), functional parts (15a) for implementing a gripping operation, a holding operation, a cutting operation, or the like being respectively provided at one end of the opening-closing members (15), the functional parts (15a) being opened and closed by adjusting a pressing force applied to the manipulation members (14), the opening-closing members (15), the manipulation members (14), and the elastic members (11) being configured so that the pressing force applied to the manipulation members (14) and an opening-
(Continued)

closing amount of the functional parts (15a) have a linear proportional relationship during a period in which the functional parts (15a) are operated.

17 Claims, 4 Drawing Sheets

(51) Int. Cl.
*A45D 26/00* (2006.01)
*A61B 17/30* (2006.01)
*A61B 17/00* (2006.01)
*A61B 17/29* (2006.01)

(52) U.S. Cl.
CPC ..... *A61B 17/3201* (2013.01); *A61B 2017/00738* (2013.01); *A61B 2017/2845* (2013.01); *A61B 2017/2918* (2013.01)

(58) Field of Classification Search
CPC .. A61B 2017/00738; A61B 2017/2845; A45D 26/0066
See application file for complete search history.

(56) References Cited

U.S. PATENT DOCUMENTS

| | | | | |
|---|---|---|---|---|
| 3,921,478 A | * | 11/1975 | Ygfors | A61B 17/2812 30/261 |
| 4,800,880 A | * | 1/1989 | Catalano | A61B 17/062 606/147 |
| 5,752,972 A | * | 5/1998 | Hoogeboom | A61B 17/29 606/174 |
| 5,813,417 A | * | 9/1998 | Rudolph | B26B 13/24 132/200 |
| 6,391,046 B1 | | 5/2002 | Overaker et al. | |
| 6,592,603 B2 | * | 7/2003 | Lasner | A61B 17/2841 606/174 |
| 2009/0030427 A1 | | 1/2009 | Razvi et al. | |
| 2012/0303049 A1 | | 11/2012 | Nakamura | |
| 2013/0211442 A1 | * | 8/2013 | Karim | A61B 17/3201 606/200 |

FOREIGN PATENT DOCUMENTS

| | | |
|---|---|---|
| JP | 7265555 A | 10/1995 |
| JP | 2006212280 A | 8/2006 |
| JP | 4277117 B2 | 6/2009 |
| JP | 2009118946 A | 6/2009 |
| JP | 4657508 B2 | 3/2011 |
| JP | 4823715 B2 | 11/2011 |
| JP | 201290919 A | 5/2012 |
| WO | 2004/032776 A1 | 4/2004 |

OTHER PUBLICATIONS

International Search Report for PCT/JP2012/007968, dated Jan. 15, 2013.

* cited by examiner

FIG. 3
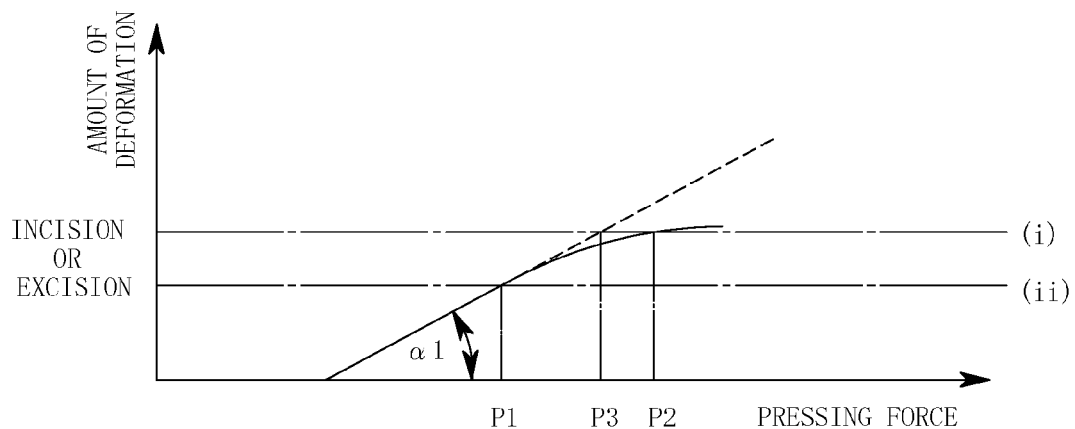
(a)
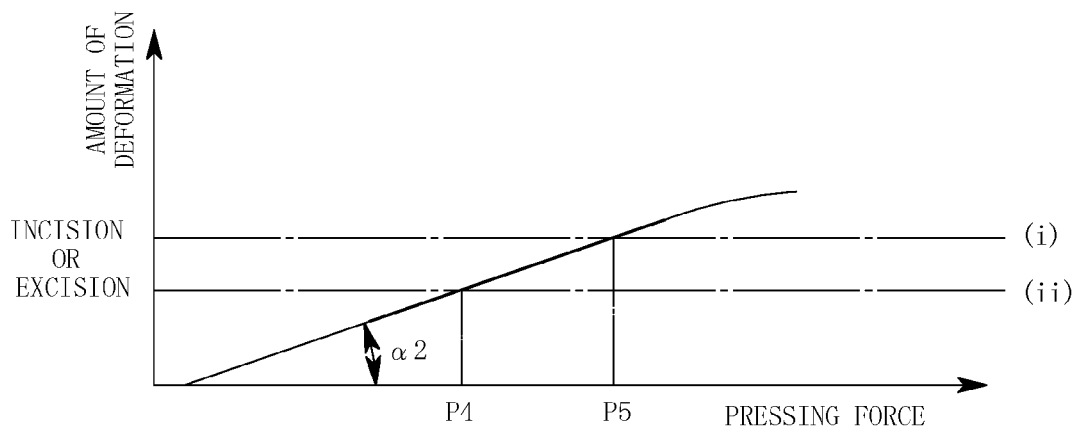
(b)

MEDICAL INSTRUMENT

The present application is a National Stage application of WIPO Application No. PCT/JP2012/007968, filed Dec. 13, 2012, naming Kaoru HORIKAWA as an inventor, the entire contents of that application being incorporated herein by reference in its entirety.

TECHNICAL FIELD

The present invention relates to a medical instrument (e.g., holder, needle holder, scissors, or tweezers) that is configured so that members are opened and closed (pivoted) around a pivot (fulcrum) to implement an incision operation, an excision operation, a gripping operation, a holding operation, a cutting operation, or the like.

BACKGROUND ART

Patent Documents 1 and 2 disclose the above type of medical instrument. Patent Documents 1 and 2 disclose a medical instrument that includes elastic members that are formed in the shape of a leaf spring, and provided at one end of the medical instrument, and opening-closing members that are provided at the other end of the medical instrument, wherein the opening-closing members intersect each other at a pivot so that the opening-closing members can be opened and closed, and a functional part that implements an incision operation, an excision operation, a gripping operation, a holding operation, a cutting operation, or the like (hereinafter referred to as "incision, excision, or the like") is provided at the end of each of the opening-closing members. The medical instrument having such a configuration makes it possible to finely adjust the motion of the functional parts by changing the pressing force applied to the elastic members, and is advantageous for surgery and the like for which a fine motion is required.

A very thin membrane, a microscopic blood vessel, a nerve, or the like may be incised or excised using scissors during heart or brain surgery, for example. In this case, body tissue situated in the vicinity of the membrane or the like may be damaged when the edge of the blade moves unintentionally even in a small amount. However, known scissors have a tendency in which the edge of the blade springs immediately after completion of incision or excision. Therefore, the user must finely adjust the force applied to the manipulation members so that the edge of the blade does not spring immediately after completion of incision or excision. This imposes a heavy burden on the user. This particularly applies to brain or heart surgery in which a very thin membrane, a microscopic blood vessel, a nerve, or the like is repeatedly incised or excised.

Patent Document 1 discloses a technique that makes it possible to adjust the spring properties of the elastic member of the medical instrument (e.g., scissors). Paragraph 0007 of Patent Document 1 states that "Operability and usage (e.g., required pressing force or hardness) when the user applies force differ depending on the repulsion force and the flexing properties of the spring 104. The repulsion force and the flexing properties of the spring 104 differ depending on the shape and the material of the spring 104, and affect operability and usage (e.g., hardness increases when titanium is used)". The surgical instrument disclosed in Patent Document 1 is configured so that the repulsion force and the flexing properties of the spring are changed by forming a plurality of grooves in the plate-like member (spring) so that the operability of the functional part can be adjusted.

However, the surgical instrument disclosed in Patent Document 1 cannot solve the problem in which the edge of the blade springs immediately after completion of incision or excision.

It is effective to use an elastic member having low spring properties (i.e., having a small modulus of elasticity) in order to prevent a situation in which the edge of the blade springs. Since the user who incises or excises a very thin membrane, a microscopic blood vessel, a nerve, or the like attaches much importance to the sensation through the edge of the blade, it is preferable that the spring properties of the elastic member be as low as possible. However, when the spring properties of the elastic member are decreased, the edge of the blade may easily move due to the weight of the manipulation member or the opening-closing member, or may not promptly return to the original position after completion of incision or excision. Therefore, the spring properties can be decreased only within a limited range.

RELATED-ART DOCUMENT

Patent Document

Patent Document 1: Japanese Patent No. 4693194
Patent Document 2: JP-A-9-140720

SUMMARY OF THE INVENTION

Technical Problem

The invention was conceived in view of the above problems. An object of the invention is to provide a medical instrument that suppresses a situation in which the edge of the blade springs immediately after completion of incision or excision, and ensures excellent operability and usage as compared with a known medical instrument.

Solution to Problem

The inventor of the invention conducted extensive studies, and found that a situation in which the edge of the blade springs occurs due to a change in the spring properties of the elastic member during incision or excision.

FIG. 3 illustrates a graph showing the relationship between the pressing force applied to the manipulation members and the amount of deformation (blade-edge opening-closing amount) measured using a known medical instrument (see (a)). As illustrated in FIG. 3 (see (a)), the spring properties of the elastic member increase during incision or excision (between the straight lines (i) and (ii)). Therefore, it is necessary to apply a pressing force P2 that is larger than a pressing force P3 that is required when a change in the spring properties of the elastic member does not occur. Specifically, the user must finely increase the pressing force applied to the manipulation members. It is considered that the above operation increases the burden imposed on the user, and leads to a situation in which the edge of the blade springs immediately after completion of incision or excision.

The inventor found that it is possible to prevent a situation in which the user must finely adjust the pressing force applied to the manipulation members corresponding to a change in spring properties, and suppress a situation in which the edge of the blade springs immediately after completion of incision or excision, by preventing a situation in which the spring properties of the elastic member change during incision or excision (see (b) in FIG. 3). This finding has led to the completion of the invention.

According to one aspect of the invention, a medical instrument includes manipulation members that are held by a user, elastic members that are respectively secured on one end of the manipulation members, and intersect each other at one end thereof, and opening-closing members that are respectively secured on the other end of the manipulation members, and intersect each other at a pivot, functional parts for implementing an incision operation, an excision operation, a gripping operation, a holding operation, a cutting operation, or the like being respectively provided at one end of the opening-closing members, the functional parts being opened and closed by adjusting a pressing force applied to the manipulation members, the opening-closing members, the manipulation members, and the elastic members being configured so that the pressing force applied to the manipulation members and an opening-closing amount of the functional parts have a linear proportional relationship during a period in which the functional parts are operated.

It is preferable that the functional parts provided to the opening-closing members be formed of a material that exhibits high sliding properties. Each of the opening-closing members may include the functional part and an opening-closing member main body, and the opening-closing member main body may be formed of a material that differs from a material that forms the functional part.

The elastic members, the manipulation members, and the opening-closing members may be formed of different metals. In this case, the functional part and the opening-closing member main body may be bonded by laser welding, and the joint between the functional part and the opening-closing member main body may be polished (ground) to remove a step. The manipulation member and the elastic member may be bonded by laser welding, and the joint between the manipulation member and the elastic member may be polished to remove a step.

It is preferable that the manipulation member and the opening-closing member be removably bonded. It is preferable that the elastic members be formed of β-titanium. Note that the elastic members may be formed of a superelastic alloy. It is preferable that the manipulation members be formed of pure titanium, and the elastic members be formed of β-titanium.

The center-of-gravity position of the medical instrument when the user holds the manipulation members may be adjusted by a combination of the weight, the length, and the shape of the manipulation members, the opening-closing members, and the elastic members.

Advantageous Effects of the Invention

According to one aspect of the invention, since the pressing force applied to the manipulation members and the opening-closing amount have a linear proportional relationship during a period in which the functional parts are operated, the user can complete incision, excision, or the like by applying a constant pressing force. Therefore, it is unnecessary for the user to finely adjust the pressing force during incision, excision, or the like. It is also possible to suppress a situation in which the edge of the blade springs after completion of incision, excision, or the like.

BRIEF DESCRIPTION OF DRAWINGS

FIG. 3 illustrates a graph showing the relationship between the pressing force and the amount of deformation measured using a known medical instrument (see (a)), and a graph showing the relationship between the pressing force and the amount of deformation measured using a medical instrument according to one embodiment of the invention (see (b)).

REFERENCE LIST 1, 1' Medical instrument
11 Elastic member
13 Pivot
14 Manipulation member
15 Opening-closing member
15a Blade
16 Fastening means

DESCRIPTION OF EMBODIMENTS

A medical instrument according to exemplary embodiments of the invention is described in detail below with reference to the drawings.

Figure 1:
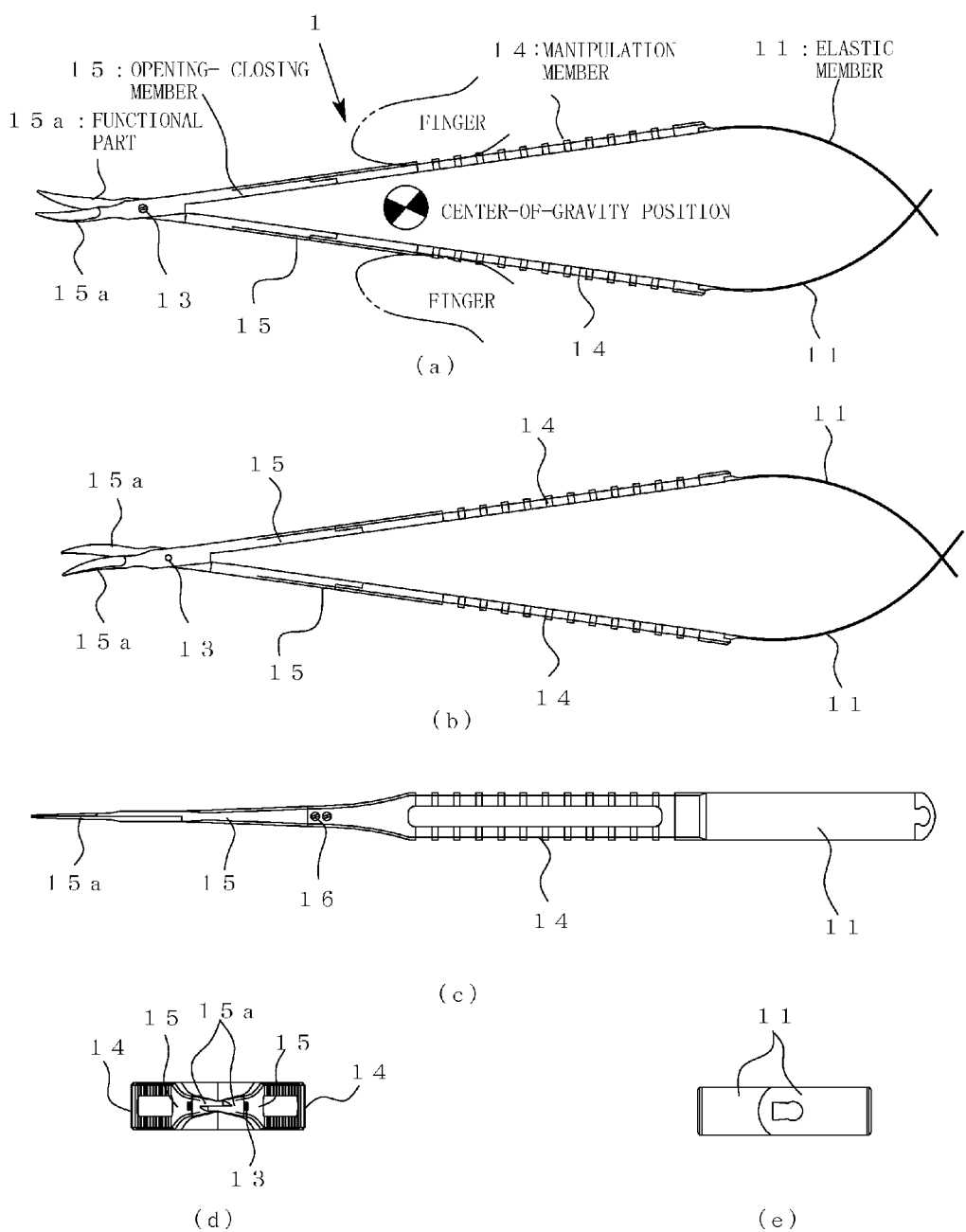
FIG. 1 illustrates a medical instrument according to one embodiment of the invention, wherein (a) is a plan view, (b) is a bottom view, (c) is a front view, (d) is a left side view, and (e) is a right side view illustrating the overall configuration of the medical instrument.

FIG. 1 illustrates a medical instrument (medical instrument 1) according to one embodiment of the invention, wherein (a) is a plan view, (b) is a bottom view, (c) is a front view, (d) is a left side view, and (e) is a right side view illustrating the overall configuration of the medical instrument 1.

An example in which the medical instrument 1 is scissors that are used to incise or excise body tissue during surgery or the like is described below. Note that the medical instrument according to the embodiments of the invention may also be applied to a holding instrument for holding a suture or body tissue, a holder, a needle holder, or tweezers for performing a holding operation or a cutting operation, and the like.

As illustrated in FIG. 1, the medical instrument 1 includes two manipulation members 14 that are held by the user (e.g., doctor), two plate-shaped elastic members 11 that are respectively secured on one end of the two manipulation members 14, and two opening-closing members 15 that are respectively secured on the other end of the two manipulation members 14. A blade 15a (i.e., functional part) is formed at one end of each of the opening-closing members 15, and the elastic members 11 are connected to each other (engage each other) at one end thereof.

The opening-closing members 15 are pivotally connected to each other through a pivot 13 in the vicinity of the blades 15a.

The manipulation members 14 are preferably formed of pure titanium that is lightweight and exhibits high strength and excellent corrosion resistance, and the elastic members 11 are preferably formed of β-titanium that exhibits excellent spring properties. The manipulation member 14 and the elastic member 11 may be bonded by laser welding or the like. It is preferable to polish the joint between the manipulation member 14 and the elastic member 11 after bonding in order to remove a step.

It is preferable to form a hole, a groove, or irregularities on the surface of the manipulation members 14 in order to provide the manipulation members 14 with non-slip properties, or decorate the manipulation members 14.

The elastic members 11 are formed in the shape of a leaf spring. The thickness of the elastic members 11 is adjusted so that the blade-edge opening-closing amount of the opening-closing members 15 and the pressing force applied to the manipulation members 14 have a linear proportional relationship.

FIG. 3 illustrates a graph showing the relationship between the pressing force and the amount of deformation measured using a commercially available product that is similar to the medical instrument 1 according to one embodiment of the invention (see (a)). The commercially available product has a configuration in which the elastic member is formed of stainless steel.

When using the commercially available product, the pressing force and the amount of deformation have a non-linear (curved) relationship immediately after the start of incision or excision, and incision or excision is performed while increasing the pressing force.

FIG. 3 also illustrates a graph showing the relationship between the pressing force and the amount of deformation that is achieved by the medical instrument 1 according to one embodiment of the invention (see (b)). The thickness and the length of the elastic members 11 are selected so that the linear relationship between the pressing force and the amount of deformation does not change during incision or excision (see (b) in FIG. 3) when the elastic members 11 are combined with the manipulation members 14 and the opening-closing members 15.

The elastic members 11 are designed to have spring properties (determined by a slope at an angle α) that ensure that a change in pressing force "P4 to P5" during incision or excision (see (b) in FIG. 3) is almost equal to a change in pressing force "P1 to P2" during incision or excision (see (a) in FIG. 3).

When β-titanium is used as the material for forming the elastic members 11, and the thickness of the elastic members 11 is about 0.20 to 0.35 mm, the length of the elastic members 11 is preferably determined to satisfy the above conditions taking account of the relationship with the opening-closing members 15 and the manipulation members 14.

The manipulation member 14 and the opening-closing member 15 are preferably bonded using a fastening means 16 such as a bolt or a rivet. It is possible to replace the opening-closing member 15 with another opening-closing member that differs in length, angle, weight, material, or the like.

The center-of-gravity position of the medical instrument 1 may be adjusted by adjusting the weight, the length, the shape, and the like of the manipulation member 14, the opening-closing member 15, and the elastic member 11. When the manipulation member 14 and the opening-closing member 15 are bonded using the fastening means 16 such as a bolt or a rivet so that the manipulation member 14 and the opening-closing member 15 can be replaced, it is possible to adjust the center-of-gravity position corresponding to the type of surgery, the surgery target part, or user's preference.

The standard center-of-gravity position of the medical instrument 1 according to one embodiment of the invention is set to be identical with (or set to a position situated forward to some extent as compared with) the position at which the user's fingers come in contact with the manipulation members 14.

The blade 15a is preferably formed of a metal material (e.g., nickel-based alloy) that is non-magnetic and exhibits excellent rust resistance, excellent wear resistance, and excellent corrosion resistance. The blade 15a may be formed integrally with the opening-closing member 15, or may be formed separately from the main body of the opening-closing member 15, and bonded to the main body of the opening-closing member 15 by laser welding, friction welding, or the like. The blade 15a and the main body of the opening-closing member 15 may be formed of similar metals, or may be formed of dissimilar metals. For example, when the blade 15a is formed of a nickel-based alloy, the main body of the opening-closing member 15 may be formed of stainless steel that is non-magnetic and exhibits excellent wear resistance and excellent corrosion resistance, for example.

Note that dissimilar metals or dissimilar alloys may be bonded using a known technique such as the method disclosed in Japanese Patent No. 4277117, Japanese Patent No. 4657508 (that is owned by the applicant of the present application), or Japanese Patent No. 4823715 (that is owned by the applicant of the present application).

According to the medical instrument 1 having the above configuration, when the user has applied pressing force in the direction in which the elastic members 11 approach each other while holding the manipulation members 14, the elastic members 11 are elastically deformed, and the blades 15a are closed around the pivot 13 (fulcrum). This makes it possible to incise or excise body tissue, for example. When the pressing force applied to the elastic members 11 has been reduced, the elastic members 11 are deformed to return to the original position, and the blades 15a are opened. According to the medical instrument 1 having the above configuration, since the opening-closing amount of the blades 15a can be finely adjusted by merely changing the pressing force applied to the elastic members 11 through the manipulation members 14, the medical instrument 1 is advantageous for incising or excising body tissue such as a very thin biomembrane, a microscopic blood vessel, or a nerve.

Figure 2:
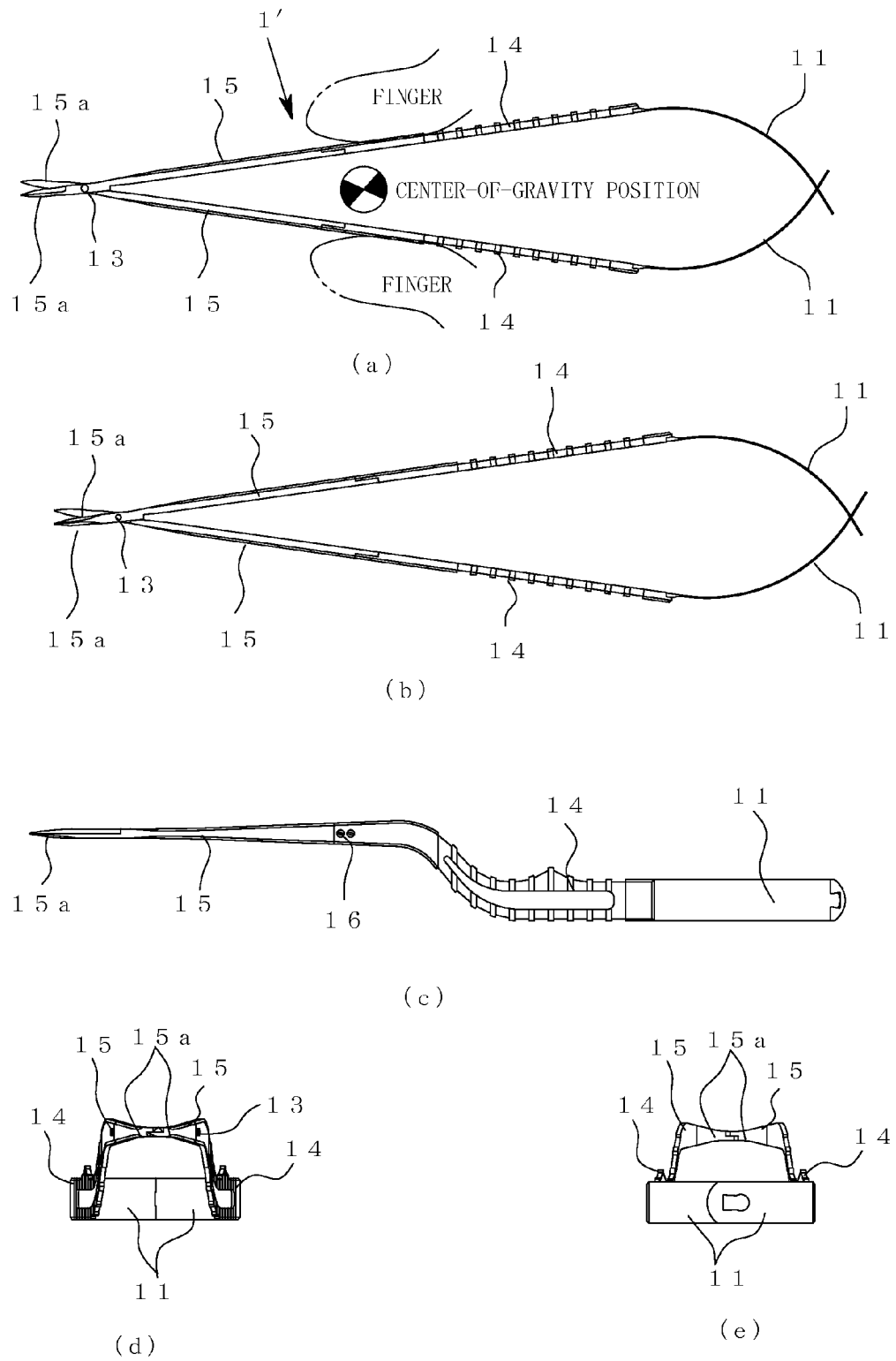
FIG. 2 illustrates a medical instrument according to another embodiment of the invention, wherein (a) is a plan view, (b) is a bottom view, (c) is a front view, (d) is a left side view, and (e) is a right side view illustrating the overall configuration of the medical instrument.

FIG. 2 illustrates a medical instrument (medical instrument 1') according to another embodiment of the invention, wherein (a) is a plan view, (b) is a bottom view, (c) is a front view, (d) is a left side view, and (e) is a right side view illustrating the overall configuration of the medical instrument 1'. In FIG. 2, the same members and the like as those illustrated in FIG. 1 are indicated by the same reference symbols. Detailed description of these members and the like is omitted.

The medical instrument 1' differs from the medical instrument 1 in that the manipulation members 14 are bent in the shape of the letter "L".

Specifically, the shape, the length, and the weight of the manipulation member 14, and the shape, the length, and the weight of the opening-closing member 15, can be arbitrarily changed corresponding to the application or user's preference.

In this case, the standard center-of-gravity position is the same as described above.

The elastic members 11 may be formed of a material other than β-titanium as long as the pressing force and the amount of deformation (blade-edge opening-closing amount) at least partially have a linear relationship, and moderate spring properties can be observed. For example, the elastic members 11 may be formed of a superelastic alloy so that the pressing force and the amount of deformation have a unique relationship.

Figure 4:
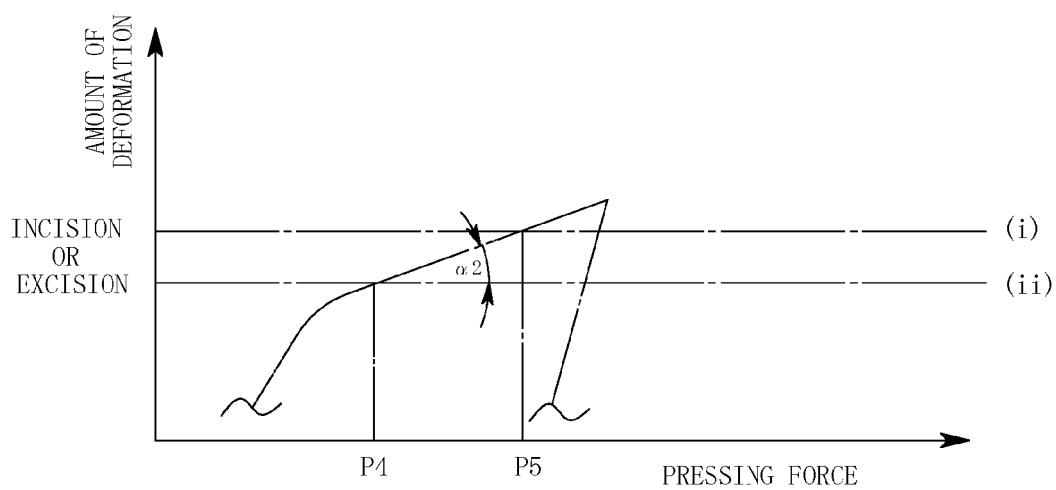
FIG. 4 illustrates a graph showing the relationship between the pressing force and the amount of deformation when a superelastic alloy is used (another embodiment of the invention).

FIG. 4 illustrates a graph showing the relationship between the pressing force and the amount of deformation when the elastic members 11 are formed of a superelastic alloy (another embodiment of the invention). As illustrated in FIG. 4, when the elastic members 11 are formed of a superelastic alloy, the pressing force and the amount of deformation have a linear relationship during incision or excision when the elastic members 11 are combined with the manipulation members 14 and the opening-closing members 15. The spring properties a during incision or excision are appropriate.

Therefore, the elastic members 11 of the medical instrument according to the embodiments of the invention may be formed of a superelastic alloy although the pressing force and the amount of deformation have a unique relationship. In this case, the elastic members 11 are preferably designed to have spring properties that ensure that a change in pressing force "P4 to P5" during incision or excision is almost equal to a change in pressing force "P1 to P2" during incision or excision (see (a) in FIG. 3).

Note that the invention is not limited to the above embodiments.

For example, the fastening means 16 is not limited to a bolt or a rivet. A rod-like shaft may be inserted into a through-hole formed in the manipulation member 14 and a through-hole formed in the opening-closing member 15, and one end or both ends of the rod-like shaft may be caulked to secure the manipulation member 14 and the opening-closing member 15.

Although an example in which the manipulation member 14 and the elastic member 11 are provided separately, and connected to each other has been described above, the manipulation member 14 and the elastic member 11 may be formed integrally, or the manipulation member 14 may form part of the elastic member 11.

INDUSTRIAL APPLICABILITY

The embodiments of the invention can be widely applied to a medical instrument (e.g., holder, needle holder, scissors, or tweezers) that is used to implement a gripping operation, a holding operation, an incision operation, an excision operation, a cutting operation, or the like.

The invention claimed is:

1. A medical instrument comprising:
    manipulation members configured to be held by a user,
    elastic members that are respectively secured on one end of the manipulation members, and intersect each other at one end thereof, and
    opening-closing members that are respectively secured on the other end of the manipulation members, and intersect each other at a pivot, functional parts configured for implementing an incision operation, an excision operation, a gripping operation, a holding operation, or a cutting operation being respectively provided at one end of the opening-closing members, the functional parts being opened and closed by adjusting a pressing force applied to the manipulation members,
    the opening-closing members, the manipulation members, and the elastic members being configured so that the pressing force applied to the manipulation members and an opening-closing amount including deformation of the functional parts have a linear proportional relationship during a period in which the functional parts are operated,
    wherein the opening-closing members, the manipulation members, and the elastic members are respectively formed of different metals.

2. The medical instrument according to claim 1, wherein the functional parts provided to the opening-closing members are formed of a material that exhibits high sliding properties.

3. The medical instrument according to claim 2, wherein each of the opening-closing members includes the corresponding functional part and an opening-closing member main body, and each opening-closing member main body is formed of a material that differs from a material that forms the corresponding functional part.

4. The medical instrument according to claim 3, wherein a respective functional part and a respective opening-closing member main body have been bonded by laser welding, and a joint between the respective functional part and the respective opening-closing member main body has been polished to remove a step.

5. The medical instrument according to claim 1, wherein a respective manipulation member and a respective elastic member have been bonded by laser welding, and a joint between the respective manipulation member and the respective elastic member has been polished to remove a step.

6. The medical instrument according to claim 1, wherein a respective manipulation member and a respective opening-closing member have been removably bonded.

7. The medical instrument according to claim 1, wherein the elastic members are formed of β-titanium or a superelastic alloy.

8. The medical instrument according to claim 1, wherein the manipulation members are formed of pure titanium, and the elastic members are formed of β-titanium.

9. The medical instrument according to claim 1, wherein a center-of-gravity position of the medical instrument when the user holds the manipulation members has been adjusted by a combination of a weight, a length, and a shape of the manipulation members, the opening-closing members, and the elastic members.

10. The medical instrument of claim 1, further comprising:
    fastening members detachably attaching the opening-closing members to the manipulation members, respectively,
    wherein each of the opening-closing members has the one end provided with the functional part and the other end detachably attached to the other end of the corresponding manipulation member through the corresponding fastening member.

11. The medical instrument of claim 10, wherein:
    each of the opening-closing members further includes the corresponding functional part and an opening-closing member main body,
    each opening-closing member main body includes the one end provided with the corresponding functional part and the other end detachably attached to the other end of the corresponding manipulation member through the corresponding fastening member, and
    each opening-closing member main body is formed of a metal different from that of the corresponding functional part.

12. A medical instrument, comprising:
a first and second manipulation member configured to be held by a user;
at least one elastic component that is respectively secured to one of the first or second manipulation members; and
a functional apparatus configured to implement at least one of an incision operation, an excision operation, a gripping operation, a holding operation or a cutting operation,
wherein the functional apparatus includes components that are opened and closed by adjusting a pressing force applied to at least one of the first or second manipulation members,
wherein the first and second manipulation members are part of respective structures that intersect each other at a pivot,
wherein the medical instrument is configured so that a pressing force applied to the manipulation members and an opening-closing amount including deformation of the functional apparatus have a linear proportional relationship during a period in which the functional apparatus is operated, and
wherein the functional apparatus, the first and second manipulation members, and the at least one elastic component are respectively formed of different metals.

13. The medical instrument according to claim 12, wherein at least one of the manipulation members and the elastic component have been bonded by laser welding, and a joint between the at least one manipulation member and the elastic component has been polished to remove a step.

14. The medical instrument according to claim 12, wherein the elastic component is formed of β-titanium or a superelastic alloy.

15. A medical instrument, comprising:
manipulation members that are configured to be held by a user and movable relative to one another, linked to a functional apparatus and to an elastic apparatus, the functional apparatus being configured for implementing at least one of an incision operation, an excision operation, a gripping operation, a holding operation or a cutting operation, wherein
the medical instrument is configured so that a pressing force applied to the manipulation members causing relative movement of the manipulation members and a closing amount including deformation of the functional apparatus have a linear proportional relationship during a period in which the functional apparatus is operated and
the manipulation members the functional apparatus, and the elastic apparatus are respectively formed of different metals.

16. The medical instrument of claim 15, wherein:
the period in which the functional apparatus is operated corresponds to operation from at least a substantially fully opened position of the functional apparatus to at least a substantially fully closed position of the functional apparatus.

17. The medical instrument of claim 15, wherein:
the period in which the functional apparatus is operated corresponds to operation from a fully opened position of the functional apparatus to a fully closed position of the functional apparatus.

* * * * *